US00PP35191P2

(12) United States Plant Patent
Hansen

(10) Patent No.: US PP35,191 P2
(45) Date of Patent: May 23, 2023

(54) ***HEUCHERELLA* PLANT NAMED 'COPPER KING'**

(50) Latin Name: X ***Heucherella* (*Heuchera* x *Tiarella*)**
Varietal Denomination: Copper King

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,785

(22) Filed: Nov. 22, 2022

(51) Int. Cl.
*A01H 5/02* (2018.01)
*A01H 6/80* (2018.01)

(52) U.S. Cl.
USPC ..... Plt./441

(58) Field of Classification Search
USPC ..... Plt./263.1, 441
See application file for complete search history.

(56) References Cited

U.S. PATENT DOCUMENTS

PP31,433 P2 * 2/2020 Hansen ..... A01H 6/80
Plt./440

* cited by examiner

*Primary Examiner* — Karen M Redden

(57) ABSTRACT

The new hybrid X *Heucherella* plant named 'Copper King' with slightly-cupped leaves at the petiole and flat margins, deeply incised into five to seven main lobes with each individual lobes irregularly incised. Foliage color starts in the spring as bright orange with reddish-copper in surrounding the veins, and the edges develop a yellowish-chartreuse and matures in the late fall to a medium-green with a mahogany pattern around the veins. 'Copper King' is vigorous and produces many airy panicles with numerous sterile creamy-white flowers in densely branched panicles beginning late spring and exhibits good heat and humidity tolerance. The plant is useful for landscaping as a specimen color, en masse, or as a container plant.

1 Drawing Sheet

Botanical denomination: X *Heucherella* (*Heuchera* x *Tiarella*).

Cultivar designation: 'Copper King'.

STATEMENT REGARDING PRIOR DISCLOSURES UNDER 37 CFR 1.77(B)(6)

The first public information of the claimed plant, in the form of a non-enabling photograph and brief description, was on a website operated by Walters Gardens, Inc. first accessible on Dec. 1, 2021. This was followed by a small photograph and brief description in the "Walters Gardens 2022-2023 Catalog" first distributed on Jun. 8, 2022. The first sale of the new plant was on Aug. 22, 2022, from Walters Gardens, Inc. to Sebright Gardens. Walters Gardens, Inc. obtained the new plant and all information about the new plant from the inventor. No plants of x *Heucherella* 'Copper King' have been sold in this country or anywhere in the world, nor has any disclosure of the new plant been made, more than one year prior to the filing date of this application, and such sale or disclosure within one year was either derived directly or indirectly from the inventor and thus should be considered a 35 U.S.C. §102(b) exception.

BACKGROUND OF THE INVENTION

The present invention relates to a new and distinct intergeneric hybrid between Coral Bells and Foam Flower, both in the Saxifragaceae family and given the cultivar name of 'Copper King' with the combined generic epithet x *Heucherella*. x *Heucherella* 'Copper King' resulted from an intentional cross between a proprietary unreleased hybrid known as *Heuchera* 15-106-116 (not patented) as the female or seed parent and *Tiarella* 'Cutting Edge' U.S. Plant Pat. No. 29,745 as the male or pollen parent. The cross was hybridized by the inventor at a wholesale perennial nursery in Zeeland, Mich., USA on Jan. 24, 2017. The new plant was selected from among many other crosses and x *Heucherella* seedlings growing at the same nursery which met the rigorous criteria of excellent foliage, vigor, and habit and was assigned the breeder code of 17-4-4.

x *Heucherella* 'Copper King' has been asexually propagated initially by basal cuttings in 2019 at a nursery in Zeeland, Mich., and by sterile tissue culture propagation. The resultant asexually propagated plants have remained stable and exhibit the same characteristics as the original plant over multiple generations.

BRIEF SUMMARY OF THE INVENTION x *Heucherella* 'Copper King' differs from its parents as well as all other X *Heucherella* known to the applicant. The most similar cultivars are x *Heucherella* 'Sweet Tea' U.S. Plant Pat. No. 21,296, 'Pumpkin Spice' U.S. Plant Pat. No. 29,925, 'Brass Lantern' U.S. Plant Pat. No. 22,396 and 'Hopscotch' U.S. Plant Pat. No. 28,750.

The female parent, *Heuchera* 15-106-116, the new plant has large rounded leaves with a brownish-green color and less dissected lobes. The male parent, 'Cutting Edge', has more dissected and narrower leaf lobes, and the foliage color is dark burgundy in the lobe centers and medium green around the lobe edges.

'Sweet Tea' has smaller foliage, that has a crenate margin, and the leaf is more reddish with a dark maroon center surrounding the veins. 'Pumpkin Spice' has smaller leaves, leaf margins that are more crenate, leaf lobes that are more rounded and less acute, and the foliage color is more reddish-bronze. 'Brass Lantern' has foliage that is more glossy in the spring, lobes have less divided sub-lobes, and the color is a duller brassy color with greyed-purple in the lobe centers. 'Hopscotch' has leaves that emerge more reddish with dark red centers. The new plant has a larger habit than all of the above varieties.

The new plant differs from all Heuchera, x *Heucherella*, and *Tiarella* known to the inventor in the following combined traits:

1. The foliage is bright orange with reddish-copper in surrounding the veins, and the edges develop a yellowish-chartreuse color;
2. Leaves mature by late fall to a medium-green with a mahogany pattern around the veins;
3. The leaf blades are slightly cupped at petiole with flat margins and deeply incised into five to seven main lobes with each individual lobes irregularly incised;
4. The flowers are creamy-white on densely branched panicles;
5. Habit is mounded with multiple tightly clustered shoots emerging at the base all season;
6. The plant is more robust, and more heat tolerant than typical x *Heucherella*.

BRIEF DESCRIPTION OF THE DRAWING

The photographs of the new plant demonstrate the overall appearance of the plant including the unique traits. The plant in the photograph is a two-year-old plant grown at a wholesale perennial nursery in Zeeland, Mich., USA. The colors are as accurate as reasonably possible with color reproductions. Some slight variations of color may occur as a result of lighting quality, intensity, wavelength, and direction or reflection.

DETAILED BOTANICAL DESCRIPTION

Figure 1:
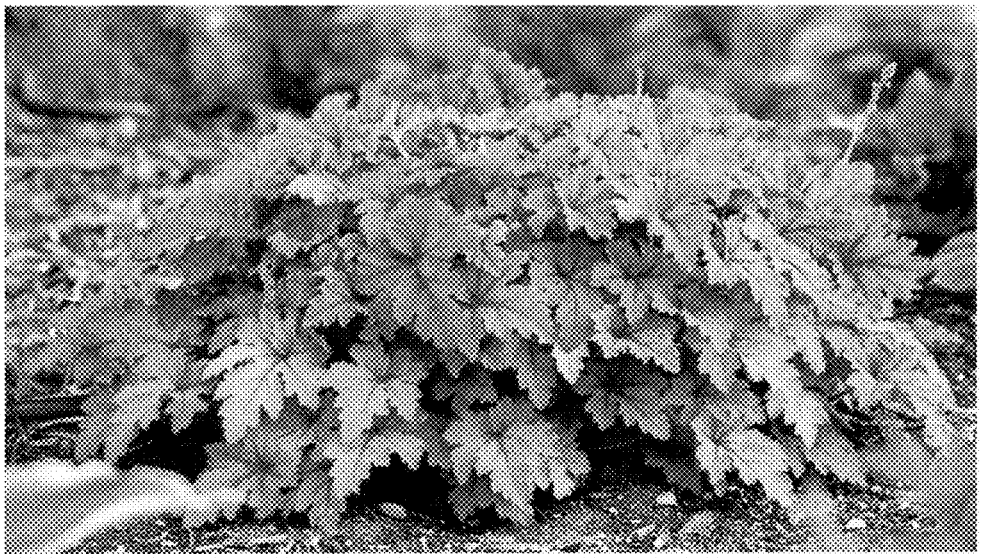
FIG. 1 shows the new plant in late spring.
Figure 2:
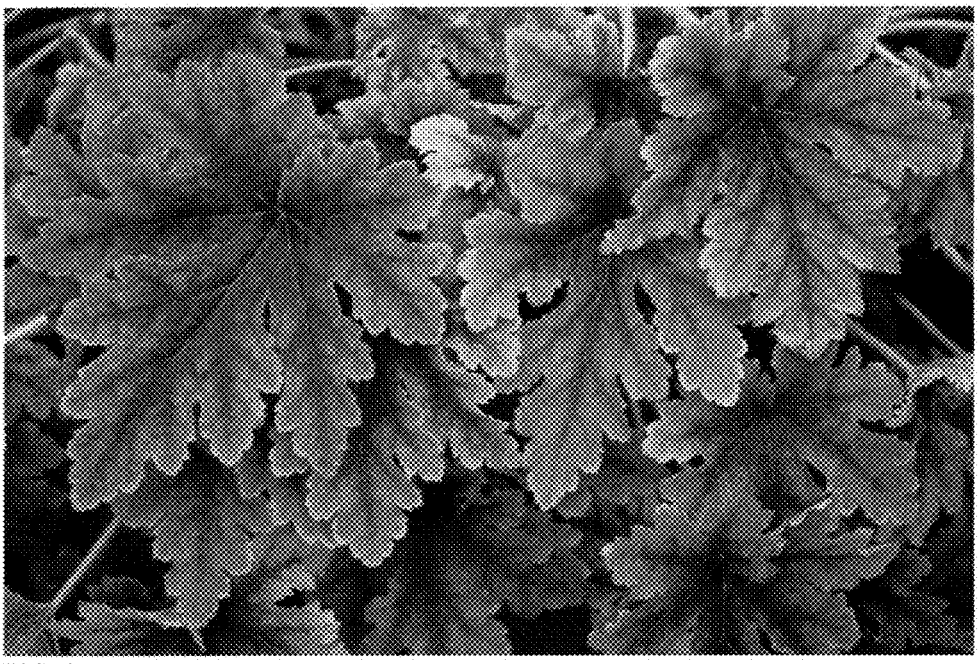
FIG. 2 shows a close-up of the foliage in mid-summer.

The following description is based on three-year-old plants growing in a partially shaded garden with supplemental water and fertilizer at a wholesale perennial nursery in Zeeland, Mich., USA. 'Copper King' has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The female or seed parent, 15-106-116, consists of genes from 'Paprika' U.S. Plant Pat. No. 24,575, 'Mocha' U.S. Plant Pat. No. 18,386 and a proprietary selection of *Heuchera hallii*; the male or pollen parent was *Tiarella* 'Cutting Edge';

Plant habit: Hardy herbaceous perennial of tightly compact rhizomes with basal rosette of mounded foliage; foliage about 30 cm tall and 90 cm across;

Roots: Fibrous, finely branched; when actively growing near white in color depending on soil type, nearest RHS 158D;

Growth rate: Rapid, rooting from cutting in 2 weeks and finishing in a three-liter container in about 3 months;

Foliage: Palmately lobed into five to seven irregular lobes; pubescent abaxial and adaxial; lobes moderately dissected to about three-quarters of the way to petiole; individual lobes are dissected to nearly halfway to primary veins; matte surface above and below; lobe further dissected apices acute to acuminate; margins ciliolate and serrate; cordate base with lobes imbricate about 1 cm; cauline leaves on up to first four nodes below flowers and decreasing in size distally; foliage density dense;

Foliage size: Blade to about 15 cm long and 14 cm wide, average about 8.5 cm long and 9 cm wide; center lobe about 6.5 cm long and about 8 cm wide; cauline leaves to 15 mm long and 17 mm wide;

Foliage margin indentations: Moderately lobed;

Foliage color: Seasonally variable; spring young emerging leaves adaxial between RHS 195A and RHS 199B toward margin portions and the center inner palm surrounding the main veins nearest RHS 187A; abaxial spring emerging leaves nearest RHS 183D; when first flowering adaxial margin portion nearest RHS 183A with variable undertone of nearest RHS 148B and center portion surrounding the veins nearest RHS 187A; when first flowering abaxial nearest RHS 183D; late fall and winter adaxial area surrounding veins nearest RHS N187A, margin portion blushed irregularly with between RHS 183A and RHS N186C, and area between veins nearest RHS 137B; late fall and winter abaxial variable, portions around edges between RHS 187B and RHS 187C with light undertone of nearest RHS 147B, portion surrounding the veins nearest RHS 183B with undertone of nearest RHS 148B, portion between the veins nearest RHS 147B and also nearest RHS 147B with slight blush of nearest RHS 187C;

Leaf margin: Serrate as juvenile and crenate when mature, ciliate;

Leaf apex: Acute as juvenile and rounded to apiculate when mature;

Leaf base: Cordate with lobes sometimes imbricate by about 1 cm;

Leaf surface: Slightly cupped at petiole; flat margins; hispidulous to sparsely pubescent adaxial and abaxial;

Leaf quantity: About six per division and 90 per plant;

Veins: Palmate, puberulent adaxial, pubescent abaxial;

Vein color: Adaxial early season nearest RHS 176C, abaxial early season main veins between RHS 146D and RHS 145A, secondary veins nearest N186C; flowering season adaxial between RHS 195A and RHS 177D, proximally and distally nearest RHS 183A, flowering season abaxial between RHS 146D and RHS 145B, secondary veins nearest N186C; late fall and winter season adaxial nearest RHS 187B in the center portion, and distally between RHS 148A and RHS 148B; and winter season abaxial primary proximal veins between RHS 146D and RHS N148B, and distal veins nearest RHS 187A;

Petiole: Cylindrical, hirsutulous, to about 25 cm long and 4 mm diameter above stipule; wiry but flexible;

Petiole color: On emerging foliage nearest RHS 187B and in the distal 3 cm between RHS 146D and RHS 195A; mid-flowering season nearest RHS 187B, and late fall and winter blend between RHS 183B and RHS 146D;

Inflorescence: In open branched panicle, about 12 panicles per plant; to about 170 flowers per panicle; first panicle flowering beginning late May in Michigan and remaining in flower for about three weeks; repeat panicles until early fall; individual flowers remaining open about three to four days; plant remains in flower with new panicles for about ten weeks;

Fragrance: None detected;

Peduncle: Cylindrical; hirsutulous to pubescent with hairs to about 2 mm long; to about 79 cm tall and 3 mm diameter at base, flowering portion about 31 cm tall and 4.5 cm wide; with cauline leaves at lower two to four nodes; upright; flower density medium;

Peduncle color: Between RHS N148B and RHS 146D below foliage and developing between RHS 182A and RHS 182C in distal region;

Peduncle branches: To about 40 per panicle; short and densely flowered; lowest branches with about 6 flowers; to about 4 cm long and 1 mm diameter; distally decreasing in size and flower quantity;

Cauline leaves: To about 15 mm long and 17 mm wide; with petioles about 10 mm long and 1 mm diameter at base, decreasing distally; color of cauline leaves and petioles same as other foliage;

Pedicel: Cylindrical; glandular to puberulent; about 2 mm long and 0.7 mm diameter;

Pedicel color: Between RHS 182C and RHS 184C;

Buds one day prior to opening: Oblong, about 3.5 mm long and 2 mm diameter;

Bud color: Distal two-thirds nearest RHS 155A, proximal portion between RHS 181C and RHS 185D;

Flower: Perfect; campanulate; about 5 mm deep and 4 mm in diameter at face; individual flowers lasting about four to five days on plant or as cut flower; attitude outwards to slightly drooping;

Calyx: Five sepals; about 4 mm across and 3 mm deep; fused in basal 2 mm into hypanthium;

Sepals: Glabrous adaxial, glandular abaxial; apex acute, margin entire; calyx about 3 mm long and 1 mm wide;

Calyx color: Adaxial and abaxial between RHS 181C and RHS 185D;

Petals: Typically, five; spatulate, narrowly acute apex, attenuate base; margin entire; minutely pubescent abaxial and glabrous adaxial; about 5 mm long and 0.8 mm wide;

Petal color: Abaxial nearest RHS NN155C; adaxial nearest RHS NN155C;

Androecium:

*Filaments*.—Typically, five, thin, about 5mm long and less than 0.3 mm in diameter; color nearest RHS NN155C.

*Anthers*.—Vestigial; oblong to nearly 0.5 mm long and about 0.2 mm wide; color nearest RHS 158A.

*Pollen*.—Not observed.

Gynoecium:

*Pistil*.—One central two-beaked pistil, about 5 mm long and 1.5 mm at base narrowing to 0.2 mm at apex; color nearest RHS N170D.

*Stigma*.—Minute, about 0.2 mm diameter; color nearest RHS 155D.

*Ovary*.—Two carpels; apex tapering to meet pistil; rounded base and sides; about 1.5 mm across at widest point at base and 2 mm tall; color nearest RHS N170D.

Fruit: Two-beaked capsule, about 4 mm long and 2 mm in diameter at widest portion; color nearest RHS 200A when mature;

Seed: Not observed;

Growth conditions: X *Heucherella* 'Copper King' grows best with ample moisture and drainage in either filtered or part sun. Cold hardy from USDA zones 4 to 9. x *Heucherella* 'Copper King' is able to tolerate heat and humidity better than many *Heucherella*.

Disease and pest tolerance: Other pest and disease resistance and tolerance outside of that normal for x *Heucherella* is not known. The new plant may be susceptible to diseases and pests common to other X *Heucherella*.

It is claimed:

1. The new and distinct ornamental plant named x *Heucherella* 'Copper King' as herein described and illustrated.

* * * * *